(12) United States Patent
Falco et al.

(10) Patent No.: US 6,355,462 B1
(45) Date of Patent: Mar. 12, 2002

(54) DISEASE RESISTANCE FACTOR

(75) Inventors: Saverio Carl Falco, Arden; Omolayo O. Famodu, Newark, both of DE (US); Feng Han, Johnston, IA (US); J. Antoni Rafalski, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/433,248

(22) Filed: Nov. 4, 1999

Related U.S. Application Data
(60) Provisional application No. 60/107,242, filed on Nov. 5, 1998.

(51) Int. Cl.⁷ .............................. C12N 9/02; C12N 1/20; C12N 15/00; C07H 21/04
(52) U.S. Cl. ................. 435/189; 435/252.3; 435/254.1; 435/255.1; 435/320.1; 536/23.2; 536/23.4; 536/23.7
(58) Field of Search .............................. 435/69.1, 320.1, 435/252.3, 189, 325, 419; 536/23.1, 23.2, 23.4, 23.7

(56) References Cited

PUBLICATIONS

Sptrembl Database, Accession No. 064743, Rounsley et al., Aug. 1, 1998.*
Sptrembl database, Accession No. P93479, Facchini et al., May 1, 1997.*
Staskawicz et al. (1995) Science 268:661–667.
Baker et al. (1997) Science 276:726–733.
Ryals et al. (1996) Plant Cell 8:1809–1819.
Hammond–Kosack and Jones (1996) Plant Cell 8:1773–1791.
Ward et al. (1991) Plant Cell 3:1085–1094.
Dittrich and Kutchan (1991) Proc. Natl. Acad. Sci. 88:9969–9973.
NCBI General Identifier No. 5262776.
Abdulla et al., Tetrahedron, 35, 1675 (1975).
Beck et al., J. Heterocyclic Chem., 24, 693 (1987).
Beck et al., J. Heterocyclic Chem., 24, 739 (1987).
Bartnik, et al., Tet. Letters 37, 8751 (1996).

\* cited by examiner

*Primary Examiner*—Rebecca E. Prouty
*Assistant Examiner*—Manjunath N. Rao

(57) ABSTRACT

This invention relates to an isolated nucleic acid fragment encoding a berberine-bridge-forming enzyme. The invention also relates to the construction of a chimeric gene encoding all or a portion of the berberine-bridge-forming enzyme, in sense or antisense orientation, wherein expression of the chimeric gene results in production of altered levels of the berberine-bridge-forming enzyme in a transformed host cell.

17 Claims, No Drawings

DISEASE RESISTANCE FACTOR

This application claims priority benefit of U.S. Provisional Application No. 60/107,242 filed Nov. 5, 1998, now pending.

FIELD OF THE INVENTION

This invention is in the field of plant molecular biology. More specifically, this invention pertains to nucleic acid fragments encoding berberine-bridge-forming enzyme in plants and seeds.

BACKGROUND OF THE INVENTION

Pathogens annually cause billions of dollars in damage to crops worldwide. Consequently, an increasing amount of research has been dedicated to developing novel methods for controlling plant diseases. Such studies have centered on the plant's innate ability to resist pathogen invasion in an effort to support the plant's own defenses to counter pathogen attacks (Staskawicz et al. (1995) *Science* 268:661–667; Baker et al. (1997) *Science* 276:726–733). One such defense mechanism under study is known as systemic acquired resistance (SAR; reviewed in Ryals et al. (1996) *Plant Cell* 8:1809–1819). SAR is defined as a generalized defense response, which is often induced by avirulent pathogens and provides enhanced resistance to a broad spectrum of virulent pathogens. Avirulent pathogens carry an avirulence (avr) gene whose product can be recognized by the product of a corresponding resistance (R) gene carried by plants. Such recognition triggers both a programmed cell death response, known as the hypersensitive response (HR), around the point of pathogen infection and release of a systemic SAR-inducing signal (Hammond-Kosack and Jones (1996) *Plant Cell* 8:1773–1791). After a rapid, localized HR, the elevated state of resistance associated with SAR is effective throughout the plant for a period of time ranging from several days to a few weeks. Coinciding with the onset of SAR is the transcriptional activation of the pathogenesis-related (PR) genes. These genes encode proteins that exhibit antimicrobial activities (Ward et al. (1991) *Plant Cell* 3:1085–1094).

The berberine bridge-forming enzyme ((S)-reticuline:oxygen oxidoreductase (methylene-bridge-forming); EC 1.5.3.9) is a vesicular plant enzyme that catalyzes the formation of the berberine bridgehead carbon of (S)-scoulerine from the N-methyl carbon of (S)-reticuline in a specific, unparalleled reaction along the biosynthetic pathway that leads to benzophenanthridine alkaloids. Cytotoxic benzophenanthridine alkaloids are accumulated in certain species of Papaveraceae and Fumariaceae in response to pathogenic attack and, therefore, function as phytoalexins. The berberine bridge enzyme has been purified to homogeneity from elicited cell-suspension cultures of *Eschscholtzia californica*. The mature protein has a molecular weight of 57,352, excluding carbohydrate. The berberine bridge enzyme was heterologously expressed in a catalytically active form in *Saccharomyces cerevisiae*. Southern hybridization with genomic DNA suggests that there is only one gene for the enzyme in the *E. californica* genome. Hybridized RNA blots from elicited *E. californica* cell-suspension cultures reveals a rapid and transient increase in poly(A)+RNA levels that preceded both the increase in enzyme activity and the accumulation of benzophenanthridine alkaloids, emphasizing the integral role of the berberine bridge enzyme in the plant response to pathogens (Dittrich and Kutchan (1991) *Proc Natl Acad Sci USA* 88:9969–9973).

SUMMARY OF THE INVENTION

The present invention relates to isolated polynucleotides comprising a nucleotide sequence encoding a first polypeptide of at least 25 amino acids that has at least 70% identity based on the Clustal method of alignment when compared to a polypeptide selected from the group consisting of a corn berberine-bridge-forming enzyme polypeptide of SEQ ID NO:2, a rice berberine-bridge-forming enzyme polypeptide of SEQ ID NO:4, a soybean berberine-bridge-forming enzyme polypeptide of SEQ ID NO:6, and a wheat berberine-bridge-forming enzyme polypeptide of SEQ ID NO:8. The present invention also relates to an isolated polynucleotide comprising the complement of the nucleotide sequences described above.

It is preferred that the isolated polynucleotide of the claimed invention consists of a nucleic acid sequence selected from the group consisting of SEQ ID NOs:1, 3, 5, and 7 that codes for the polypeptide selected from the group consisting of SEQ ID NOs:2, 4, 6, and 8. The present invention also relates to an isolated polynucleotide comprising a nucleotide sequences of at least 30 (preferably at least 40) contiguous nucleotides derived from a nucleotide sequence selected from the group consisting of SEQ ID NOs:1, 3, 5, and 7 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a berberine-bridge-forming enzyme polypeptide of at least 25 amino acids comprising at least 70% homology based on the Clustal method of alignment compared to a polypeptide selected from the group consisting of SEQ ID NOs:2, 4, 6, and 8.

The present invention relates to a method of selecting an isolated polynucleotide that affects the level of expression of a berberine-bridge-forming enzyme polypeptide in a host cell, preferably a plant cell, the method comprising the steps of:

constructing an isolated polynucleotide of the present invention or an isolated chimeric gene of the present invention;

introducing the isolated polynucleotide or the isolated chimeric gene into a host cell;

measuring the level a berberine-bridge-forming enzyme polypeptide in the host cell containing the isolated polynucleotide; and comparing the level of a berberine-bridge-forming enzyme polypeptide in the plant cell containing the isolated polynucleotide with the level of a berberine-bridge-forming enzyme polypeptide in a plant cell that does not contain the isolated polynucleotide.

The present invention relates to a method of obtaining a nucleic acid fragment encoding a substantial portion of a berberine-bridge-forming enzyme polypeptide gene, preferably a plant berberine-bridge-forming enzyme polypeptide gene, comprising the steps of: synthesizing an oligonucleotide primer comprising a nucleotide sequence of at least 30 (preferably at least) 40 contiguous nucleotides derived from a nucleotide sequence selected from the group consisting of SEQ ID NOs:1, 3, 5, 7, and the complement of such nucleotide sequences; and amplifying a nucleic acid fragment (preferably a cDNA inserted in a cloning vector) using the oligonucleotide primer. The amplified nucleic acid fragment preferably will encode a portion of a berberine-bridge-forming enzyme amino acid sequence.

The present invention also relates to a method of obtaining a nucleic acid fragment encoding all or a substantial portion of the amino acid sequence encoding a berberine-bridge-forming enzyme polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

The present invention relates to a composition comprising an isolated polynucleotide of the present invention.

The present invention relates to an isolated polynucleotide comprising the nucleotide sequence comprising at least one of 30 contiguous nucleotides of a nucleic sequence selected from the group consisting of SEQ ID NOS:1, 3, 5, and 7.

The present invention relates to an expression cassette comprising an isolated polynucleotide of the present invention operably linked to a promoter.

The present invention relates to a method for positive selection of a transformed cell comprising:

(a) transforming a plant cell, preferably a monocot such as corn, with the chimeric gene of the present invention or an expression cassette of the present invention; and (b) growing the transformed plant cell under conditions allowing expression of the polynucleotide in an amount sufficient to induce disease resistance in the plant cell to provide a positive selection means.

BRIEF DESCRIPTION OF THE SEQUENCE LISTING

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Disease Resistance Factors

| | | SEQ ID NO: | |
|---|---|---|---|
| Protein | Clone Designation | (Nucleotide) | (Amino Acid) |
| Corn berberine-bridge-forming enzyme | cco1n.pk0038.a5 | 1 | 2 |
| Rice berberine-bridge-forming enzyme | rr1.pk0047.a9 | 3 | 4 |
| Soybean berberine-bridge-forming enzyme | sls1c.pk011.i1 | 5 | 6 |
| Wheat berberine-bridge-forming enzyme | wr1.pk0028.b10 | 7 | 8 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least 30 contiguous nucleotides, preferably at least 40 contiguous nucleotides, most preferably at least 60 contiguous nucleotides, of the nucleic acid sequence of the SEQ ID NOs:1, 3, 5, and 7.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60 contiguous nucleotides derived from a nucleotide sequence selected from the group consisting of SEQ ID NOs:1, 3, 5, 7, and the complement of such nucleotide sequences may be used in methods of selecting an isolated polynucleotide that affects the expression of a polypeptide (such as berberine-bridge-forming enzyme) in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol*. 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the fimction of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several berberine-bridge-forming enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other berberine-bridge-forming enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as berberine-bridge-forming enzyme) preferably a substantial portion of a plant polypeptide of a gene, comprising the steps of: synthesizing an oligonucleotide primer comprising a nucleotide sequence of at least 30 (preferably at least 40, most preferably at least) 60 contiguous nucleotides derived from a nucleotide sequence selected from the group consisting of SEQ ID NOs:1, 3, 5, 7, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher levels than normal or in cell types or developmental stages in which they are not normally found. This would have the effect of altering the level of pathogen resistance in those cells. The berberine-bridge-forming enzyme plays an integral role in pathogen defense thus its overexpression should allow the control of crop pathogens.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptide to different cellular compartments, or to facilitate its secretion from the cell. It is thus envisioned that the chimeric gene described above may be further supplemented by altering the coding sequence to encode the instant polypeptide with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

The instant polypeptide (or portions thereof) may be produced in heterologous host cells, particularly in the cells of microbial hosts, and can be used to prepare antibodies to the these proteins by methods well known to those skilled in the art. The antibodies are useful for detecting the polypeptide of the instant invention in situ in cells or in vitro in cell extracts. Preferred heterologous host cells for production of the instant polypeptide are microbial hosts. Microbial expression systems and expression vectors containing regulatory sequences that direct high level expression of foreign proteins are well known to those skilled in the art. Any of these could be used to construct a chimeric gene for production of the instant polypeptide. This chimeric gene could then be introduced into appropriate microorganisms via transformation to provide high level expression of the encoded berberine-bridge-forming enzyme. An example of a vector for high level expression of the instant polypeptide in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---|---|---|
| cco1n | Corn Cob of 67 Day Old Plants Grown in Green House* | cco1n.pk0038.a5 |
| rr1 | Rice Root of Two Week Old Developing Seedling | rr1.pk0047.a9 |
| sls1c | Soybean Infected With *Sclerotinia sclerotiorum* Mycelium | sls1c.pk011.i1 |
| wr1 | Wheat Root From 7 Day Old Seedling | wr1.pk0028.b10 |

*This library was normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding berberine-bridge-forming enzyme were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Berberine Bridge Forming Enzyme

The BLASTX search using the EST sequences from clones listed in Table 3 revealed similarity of the polypeptides encoded by the cDNAs to berberine-bridge-forming enzyme from *Arabidopsis thaliana* (NCBI General Identifier No. 5262776). Shown in Table 3 are the BLAST results for individual ESTs ("EST"), the sequences of the entire cDNA inserts comprising the indicated cDNA clones ("FIS"), or sequences encoding the entire protein derived from an FIS ("CGS"):

TABLE 3

BLAST Results for Sequences Encoding Polypeptides Homologous to Berberine Bridge Forming Enzyme

| Clone | Status | BLAST pLog Score 5262776 |
|---|---|---|
| cco1n.pk0038.a5 | FIS | 118.00 |
| rr1.pk0047.a9 | EST | 16.30 |
| sls1c.pk011.i1 | CGS | 165.00 |
| wr1.pk0028.b10 | FIS | 27.05 |

The data in Table 4 represents a calculation of the percent identity of the amino acid sequences set forth in SEQ ID NOs:2, 4, 6, and 8 and the *Arabidopsis thaliana* sequence (NCBI General Identifier No. 5262776).

TABLE 4

Percent Identity of Amino Acid Sequences Deduced From the Nucleotide Sequences of cDNA Clones Encoding Polypeptides Homologous to Berberine Bridge Forming Enzyme

| SEQ ID NO. | Percent Identity to 5262776 |
|---|---|
| 2 | 49.6 |
| 4 | 23.4 |
| 6 | 51.6 |
| 8 | 40.3 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a corn, a rice, a soybean, and a wheat berberine-bridge-forming enzyme. These sequences represent the first corn, rice, soybean, and wheat sequences encoding berberine-bridge-forming enzyme.

Example 4

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110-2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL 1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptide in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptide. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS100/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptide can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide encoding a berberine-bridge-forming enzyme that has at least 70% sequence identity based on the Clustal method of alignment when compared to a polypeptide of SEQ ID NO:6.

2. The isolated polynucleotide of claim 1, wherein the sequence of the isolated polynucleotide is SEQ ID NO:5.

3. The isolated polynucleotide of claim 1 wherein the isolated polynucleotide is DNA.

4. The isolated polynucleotide of claim 1 wherein the isolated polynucleotide is RNA.

5. A chimeric gene comprising the isolated polynucleotide of claim 1 operably linked to at least one suitable regulatory sequence.

6. A host cell comprising the chimeric gene of claim 5.

7. An isolated host cell comprising an isolated polynucleotide of claim 1.

8. The cell of claim 7 wherein the isolated host is selected from the group consisting of yeast, bacteria, and plant.

9. A virus comprising the isolated polynucleotide of claim 1.

10. A composition comprising the isolated polynucleotide of claim 1.

11. An expression cassette comprising an isolated polynucleotide of claim 1 operably linked to a promoter.

12. The polynucleotide of claim 1 wherein the sequence identity is at least 80%.

13. The polynucleotide of claim 1 wherein the sequence identity is at least 85%.

14. The polynucleotide of claim 1 wherein the sequence identity is at least 90%.

15. The polynucleotide of claim 1 wherein the sequence identity is at least 95%.

SEQUENCE LISTING

```
<160> NUMBER OF SEQ ID NOS: 8

<210> SEQ ID NO 1
<211> LENGTH: 1386
<212> TYPE: DNA
<213> ORGANISM: Zea mays

<400> SEQUENCE: 1
gcacgaggcg cttcgccgtg ctcgacctcg ccgctttccg tgacgtccgc gtcgactccg      60
cgcgcgccga ggcgtgggct ggatcggggg ccacgctcgg cgaggtctac tatgccgtcg     120
ccgccgccag ccgcgtgctc gcgttccccg ctgggatctg ccccactgtc ggcgtaggag     180
gacacctcag cggcggcggc ttcggcacgc tgatgcgcag gtacggcctc gctgcggaca     240
acgtcattga cgccgtcctc gttgacgccg acgggaggct gctgaaccgg accaccatgg     300
gggaggacct gttctgggcc atccgcggtg gcggcgggga gagcttcggt gtcgtactgt     360
```

-continued

```
cttggaagct ccgcctcgtg cgcgtgccgg agacagtcac cgtgttcacc gtgcgccggt    420
caataaacca gtccgcctcg cacctcatca ccaaatggca ggcaatcgcg ccggcgctgc    480
ccagtgacct catcctccga gtcgccgtcc ggagccagca cgcgcggttt gaggcactgt    540
tcctcggccg ctgcagccgc ctccttgagc acatgcgagt tcacttcccc gaccttggcg    600
tcacccaatc ggactgcgag gagataagct ggatccagtc caccgtgtac ttcgccttct    660
actcgagctc caagccactg gagctgctcc tggacaggag cggcgagacg cccagatacg    720
tcaaggccaa gtccgactac gtgcaagaac ccatcccacg gcacgtgtgg gagagaacat    780
ggtcatggct ggagaagccc gacgccgggc tgctcatcct ggacccctac ggcggccgga    840
tgggcagcat ctctccgtca gcgacgccgt tcccgcaccg gaaggggaac ctgtacaacc    900
tccagtacta ctcgtattgg ttcgagaatg gcactgcggc attggagaag cggatgagct    960
gggtcagggg gctgtacgag gagatggagc cgtatgtgtc caagaaccca agaactggat   1020
atgtcaacta cagggacctg gatcttggga cgaacgagtt ggaggacaat gtgactagct   1080
acgccagggc gaggatctgg ggggagaagt atttcaaagg caattttgag aggctggcag   1140
ctgtgaaggc catggcggat cctaatgact tcttcaggaa tgagcagagc atccctcctc   1200
ttcccgctgc aaaaggatgg ggctccattt gagtggtcgt ttgtttcgta gctttgtggt   1260
ggtggatttc ttgtctacgt ttgtgaattg tgatcacggc tgaggatttg catgggtgaa   1320
gtgtagaatg cactattgta ttccgtgttc tgttgagctg agttctcttt gatttgtttt   1380
taaaaa                                                              1386
```

<210> SEQ ID NO 2
<211> LENGTH: 397
<212> TYPE: PRT
<213> ORGANISM: Zea mays

<400> SEQUENCE: 2

```
Phe Ala Val Leu Asp Leu Ala Ala Phe Arg Asp Val Arg Val Asp Ser
  1               5                  10                  15

Ala Arg Ala Glu Ala Trp Ala Gly Ser Gly Ala Thr Leu Gly Glu Val
                 20                  25                  30

Tyr Tyr Ala Val Ala Ala Ser Arg Val Leu Ala Phe Pro Ala Gly
             35                  40                  45

Ile Cys Pro Thr Val Gly Val Gly Gly His Leu Ser Gly Gly Gly Phe
         50                  55                  60

Gly Thr Leu Met Arg Arg Tyr Gly Leu Ala Ala Asp Asn Val Ile Asp
 65                  70                  75                  80

Ala Val Leu Val Asp Ala Asp Gly Arg Leu Leu Asn Arg Thr Thr Met
                 85                  90                  95

Gly Glu Asp Leu Phe Trp Ala Ile Arg Gly Gly Gly Gly Glu Ser Phe
            100                 105                 110

Gly Val Val Leu Ser Trp Lys Leu Arg Leu Val Arg Val Pro Glu Thr
            115                 120                 125

Val Thr Val Phe Thr Val Arg Arg Ser Ile Asn Gln Ser Ala Ser His
        130                 135                 140

Leu Ile Thr Lys Trp Gln Ala Ile Ala Pro Leu Pro Ser Asp Leu
145                 150                 155                 160

Ile Leu Arg Val Ala Val Arg Ser Gln His Ala Arg Phe Glu Ala Leu
                165                 170                 175

Phe Leu Gly Arg Cys Ser Arg Leu Leu Glu His Met Arg Val His Phe
            180                 185                 190
```

-continued

```
Pro Asp Leu Gly Val Thr Gln Ser Asp Cys Glu Glu Ile Ser Trp Ile
            195                 200                 205

Gln Ser Thr Val Tyr Phe Ala Phe Tyr Ser Ser Lys Pro Leu Glu
        210                 215                 220

Leu Leu Leu Asp Arg Ser Gly Glu Thr Pro Arg Tyr Val Lys Ala Lys
225                 230                 235                 240

Ser Asp Tyr Val Gln Glu Pro Ile Pro Arg His Val Trp Glu Arg Thr
                245                 250                 255

Trp Ser Trp Leu Glu Lys Pro Asp Ala Gly Leu Leu Ile Leu Asp Pro
            260                 265                 270

Tyr Gly Gly Arg Met Gly Ser Ile Ser Pro Ser Ala Thr Pro Phe Pro
            275                 280                 285

His Arg Lys Gly Asn Leu Tyr Asn Leu Gln Tyr Tyr Ser Tyr Trp Phe
        290                 295                 300

Glu Asn Gly Thr Ala Ala Leu Glu Lys Arg Met Ser Trp Val Arg Gly
305                 310                 315                 320

Leu Tyr Glu Glu Met Glu Pro Tyr Val Ser Lys Asn Pro Arg Thr Gly
                325                 330                 335

Tyr Val Asn Tyr Arg Asp Leu Asp Leu Gly Thr Asn Glu Leu Glu Asp
            340                 345                 350

Asn Val Thr Ser Tyr Ala Arg Ala Arg Ile Trp Gly Glu Lys Tyr Phe
        355                 360                 365

Lys Gly Asn Phe Glu Arg Leu Ala Ala Val Lys Ala Met Ala Asp Pro
    370                 375                 380

Asn Asp Phe Phe Arg Asn Glu Gln Ser Ile Pro Pro Leu
385                 390                 395

<210> SEQ ID NO 3
<211> LENGTH: 582
<212> TYPE: DNA
<213> ORGANISM: Oryza sativa
<220> FEATURE:
<221> NAME/KEY: unsure
<222> LOCATION: (337)
<221> NAME/KEY: unsure
<222> LOCATION: (370)
<221> NAME/KEY: unsure
<222> LOCATION: (421)
<221> NAME/KEY: unsure
<222> LOCATION: (437)
<221> NAME/KEY: unsure
<222> LOCATION: (481)
<221> NAME/KEY: unsure
<222> LOCATION: (484)
<221> NAME/KEY: unsure
<222> LOCATION: (502)
<221> NAME/KEY: unsure
<222> LOCATION: (511)
<221> NAME/KEY: unsure
<222> LOCATION: (542)
<221> NAME/KEY: unsure
<222> LOCATION: (547)
<221> NAME/KEY: unsure
<222> LOCATION: (564)
<221> NAME/KEY: unsure
<222> LOCATION: (571)

<400> SEQUENCE: 3
acatcctgaa ccggaccatc gccatggaca cctccaacaa ggccacctcc gactacgtcc      60
ggcaagccat cggcagggac acgtggagcg ccatcttcgg gtggctcgcg cggcccaacg     120
ccgggctgat gatcctggac ccgtacggcg ggcagatcgg cagcgtggcg gaggcggcga     180
```

-continued

```
cgccgttccc gcaccgcggc ggcgtgctct acaacatcca gtacatgaac ttctggagcg    240
cggcgggcgg aggcggcggc ggcgcggcgc agagggcgtg gttcagggac tctacgcgtt    300
catgggcgcc gttccgtgag caaggacccc gagggangcg ttacgccaac tacagggacc    360
tgggacctcn ggcgagaacg ttgtccgcgc cccgcggcgt caacaactac gacccggcaa    420
ngtgttgggg gaaaaantat tcaaaggggg aactaccaac ggtccccatg gccaagcgca    480
nttnacgccg acgactactt angaacaaca nacatcccgc cactgtcccg ggaaatgaca    540
ancaatnaaa tgtacatggc tacncctcgt nacataaaaa ta                        582
```

```
<210> SEQ ID NO 4
<211> LENGTH: 158
<212> TYPE: PRT
<213> ORGANISM: Oryza sativa
<220> FEATURE:
<221> NAME/KEY: UNSURE
<222> LOCATION: (112)
<221> NAME/KEY: UNSURE
<222> LOCATION: (123)
<221> NAME/KEY: UNSURE
<222> LOCATION: (140)
<221> NAME/KEY: UNSURE
<222> LOCATION: (145)

<400> SEQUENCE: 4

Ile Leu Asn Arg Thr Ile Ala Met Asp Thr Ser Asn Lys Ala Thr Ser
  1               5                  10                  15

Asp Tyr Val Arg Gln Ala Ile Gly Arg Asp Thr Trp Ser Ala Ile Phe
             20                  25                  30

Gly Trp Leu Ala Arg Pro Asn Ala Gly Leu Met Ile Leu Asp Pro Tyr
         35                  40                  45

Gly Gly Gln Ile Gly Ser Val Ala Glu Ala Ala Thr Pro Phe Pro His
     50                  55                  60

Arg Gly Gly Val Leu Tyr Asn Ile Gln Tyr Met Asn Phe Trp Ser Ala
 65                  70                  75                  80

Ala Gly Gly Gly Gly Gly Ala Ala Gln Arg Ala Trp Phe Arg Asp
                 85                  90                  95

Ser Thr Arg Ser Trp Ala Pro Phe Arg Glu Gln Gly Pro Arg Gly Xaa
            100                 105                 110

Arg Tyr Ala Asn Tyr Arg Asp Leu Gly Pro Xaa Ala Arg Thr Leu Ser
            115                 120                 125

Ala Pro Arg Gly Val Asn Asn Tyr Asp Pro Ala Xaa Cys Trp Gly Lys
        130                 135                 140

Xaa Tyr Ser Lys Gly Glu Leu Pro Thr Val Pro Met Ala Lys
145                 150                 155
```

```
<210> SEQ ID NO 5
<211> LENGTH: 1831
<212> TYPE: DNA
<213> ORGANISM: Glycine max

<400> SEQUENCE: 5
gcacgaggta acatggaat tgagttattg tgcagtgttt ctgatactgc ttattccaat      60
ctcacgtgca gatgctacat cagttgagaa gcaattcaag gaatgcttgt taacccaact    120
tgatggaaat tctgaacaca ttgaaaaaat aaccttcacc tcatcctcca cactatatcc    180
ccaagtttgg gattcattgg cacaaaatcc aagatgggtt aatatttcat caaggaagcc    240
tcttatgatt ctaacacctt tccatgaatc agaaattcaa gcagccattc tatgcagcaa    300
```

-continued

| | |
|---|---|
| agaactgaag ttgcagctaa gagtgagaag tggaggccat gattatgaag ggctatcata | 360 |
| ccttagtgat gtaccatttg tgatggttga cctgatcaac atccgttcca ttgaaattaa | 420 |
| ccttgctgat gaaacagctt ggggttcaggc tggggcatca ataggtgaac tttactacaa | 480 |
| aatttcaaaa gcaagtaaag tgcacggatt cccggcagga acctgtccaa gtgtagggat | 540 |
| aggaggacat ataagtggag ggggacaggg tctgatgttg aggaagcatg cctagcagc | 600 |
| agacaatgtt gtcgatgctt acctcataga tgcaaatggg aagattcatg atagaaaatc | 660 |
| aatgggagaa gatgttttct gggccatcag aggaggtgat gcttctagtt ttggagtcat | 720 |
| ccttgcatgg aagatcaagt tggtcagagt tccacctatt gttaccgggt tcaacgttcc | 780 |
| tagaacacct gaggaaggag tcaccgatct cattcacagg tggcaataca tagcacatga | 840 |
| cttgcatgag gatcttgtca ttagagtaat tgctcaaatt agtggccatg acaaatcaaa | 900 |
| aaaattccga gcaaccttca actctatttt cctaggagga gtagacaggt tgatcccact | 960 |
| gatgaatgag agtttccctg aattgggatt gcaggccaaa gactgcactg aaatgagctg | 1020 |
| gattcaatca gttatgttca tagctggata caacatagag gaccctctag aactcttgct | 1080 |
| caacagaact accatgttta aaagatcttt caaggccaag tctgacttct ttaaggagcc | 1140 |
| tgtaccaaaa tctggtctag aaggagcttg gaaactgctt ctagaagaag aaatagcctt | 1200 |
| cctgataatg gaaccatatg gtggtagaat gaatgaaatt tcagaatctg aaattccttt | 1260 |
| tccccacaga aagggcaact tgtacaactt acaatacttg gtcaattggg aagtgaatag | 1320 |
| cgacgaagca tccaggaggc atctacaatg ggccaaaatg gtttataaat acatgactcc | 1380 |
| ttatgtctca aaatctccta gagctgccta tttcaactat aaggatcttg atttgggcaa | 1440 |
| aaacaagctg gacagcacaa gctactcaga agctagtgtt tggggcaaga agtacttaa | 1500 |
| gggaaacttt aggagattag ctcaaattaa gacaaagttt gacccctaa atttttcag | 1560 |
| gaatgaacag agtattcctc tccttaattc ccaccattct taacattaag ggcatgatat | 1620 |
| tatttggagc atctaagaca tttgtgtagt gcttcattat cagattaatc ttctgccgtg | 1680 |
| ttattatttt gcaaacattt caagggagg ggattcaatt tcaaaatgga tatgatgtat | 1740 |
| gtggacttgt gtaacatgtc atcatgaagt tacgaaatct cgtaagaatg tacccttaag | 1800 |
| ttgcataaaa aaaaaaaaaa aaaaaaaaaa a | 1831 |

<210> SEQ ID NO 6
<211> LENGTH: 529
<212> TYPE: PRT
<213> ORGANISM: Glycine max

<400> SEQUENCE: 6

```
Met Glu Leu Ser Tyr Cys Ala Val Phe Leu Ile Leu Leu Ile Pro Ile
 1               5                  10                  15

Ser Arg Ala Asp Ala Thr Ser Val Glu Lys Gln Phe Lys Glu Cys Leu
            20                  25                  30

Leu Thr Gln Leu Asp Gly Asn Ser Glu His Ile Glu Lys Ile Thr Phe
        35                  40                  45

Thr Ser Ser Thr Leu Tyr Pro Gln Val Trp Asp Ser Leu Ala Gln
    50                  55                  60

Asn Pro Arg Trp Val Asn Ile Ser Ser Arg Lys Pro Leu Met Ile Leu
65                  70                  75                  80

Thr Pro Phe His Glu Ser Glu Ile Gln Ala Ala Ile Leu Cys Ser Lys
                85                  90                  95

Glu Leu Lys Leu Gln Leu Arg Val Arg Ser Gly Gly His Asp Tyr Glu
```

-continued

```
                100                 105                 110
Gly Leu Ser Tyr Leu Ser Asp Val Pro Phe Val Met Val Asp Leu Ile
            115                 120                 125

Asn Ile Arg Ser Ile Glu Ile Asn Leu Ala Asp Glu Thr Ala Trp Val
130                 135                 140

Gln Ala Gly Ala Ser Ile Gly Glu Leu Tyr Tyr Lys Ile Ser Lys Ala
145                 150                 155                 160

Ser Lys Val His Gly Phe Pro Ala Gly Thr Cys Pro Ser Val Gly Ile
            165                 170                 175

Gly Gly His Ile Ser Gly Gly Gln Gly Leu Met Leu Arg Lys His
            180                 185                 190

Gly Leu Ala Ala Asp Asn Val Val Asp Ala Tyr Leu Ile Asp Ala Asn
            195                 200                 205

Gly Lys Ile His Asp Arg Lys Ser Met Gly Glu Asp Val Phe Trp Ala
            210                 215                 220

Ile Arg Gly Gly Asp Ala Ser Ser Phe Gly Val Ile Leu Ala Trp Lys
225                 230                 235                 240

Ile Lys Leu Val Arg Val Pro Pro Ile Val Thr Gly Phe Asn Val Pro
            245                 250                 255

Arg Thr Pro Glu Glu Gly Val Thr Asp Leu Ile His Arg Trp Gln Tyr
            260                 265                 270

Ile Ala His Asp Leu His Glu Asp Leu Val Ile Arg Val Ile Ala Gln
            275                 280                 285

Ile Ser Gly His Asp Lys Ser Lys Lys Phe Arg Ala Thr Phe Asn Ser
            290                 295                 300

Ile Phe Leu Gly Gly Val Asp Arg Leu Ile Pro Leu Met Asn Glu Ser
305                 310                 315                 320

Phe Pro Glu Leu Gly Leu Gln Ala Lys Asp Cys Thr Glu Met Ser Trp
            325                 330                 335

Ile Gln Ser Val Met Phe Ile Ala Gly Tyr Asn Ile Glu Asp Pro Leu
            340                 345                 350

Glu Leu Leu Leu Asn Arg Thr Thr Met Phe Lys Arg Ser Phe Lys Ala
            355                 360                 365

Lys Ser Asp Phe Phe Lys Glu Pro Val Pro Lys Ser Gly Leu Glu Gly
            370                 375                 380

Ala Trp Lys Leu Leu Leu Glu Glu Ile Ala Phe Leu Ile Met Glu
385                 390                 395                 400

Pro Tyr Gly Gly Arg Met Asn Glu Ile Ser Glu Ser Glu Ile Pro Phe
            405                 410                 415

Pro His Arg Lys Gly Asn Leu Tyr Asn Leu Gln Tyr Leu Val Asn Trp
            420                 425                 430

Glu Val Asn Ser Asp Glu Ala Ser Arg Arg His Leu Gln Trp Ala Lys
            435                 440                 445

Met Val Tyr Lys Tyr Met Thr Pro Tyr Val Ser Lys Ser Pro Arg Ala
450                 455                 460

Ala Tyr Phe Asn Tyr Lys Asp Leu Asp Leu Gly Lys Asn Lys Leu Asp
465                 470                 475                 480

Ser Thr Ser Tyr Ser Glu Ala Ser Val Trp Gly Lys Lys Tyr Phe Lys
            485                 490                 495

Gly Asn Phe Arg Arg Leu Ala Gln Ile Lys Thr Lys Phe Asp Pro Leu
            500                 505                 510

Asn Phe Phe Arg Asn Glu Gln Ser Ile Pro Leu Leu Asn Ser His His
            515                 520                 525
```

```
Ser

<210> SEQ ID NO 7
<211> LENGTH: 588
<212> TYPE: DNA
<213> ORGANISM: Triticum aestivum

<400> SEQUENCE: 7
cgccggcctc atcgtgctcg agccccacgg cgggctcatg gccaccatcc ccaccgccgc      60
aacgccgtac ccgcaccgga gcggcgtgct ctacatcatc cagtacatcg cgttctggca     120
aggcgacggc ggcacggcgg ccaccacctg gctcggcagc ttctacgact tcatggggca     180
ctacgtgagc agcaacccga ggcaggcgta cgtcaacttc cgggacctgg acatcggcca     240
gaacgcggtg tcggacgacc tcagtaccac gtcccagagc ggcaaggttt ggggtgagcg     300
ctacttcatg agcaactacc agaggctcgc gtcggtgaag gcagccgtgg atccaatgga     360
ctacttcaga aacgagcaga gcatcccccc gttgcgacca gtcccagcct acaacgacta     420
caacgacgac ccaagtgagc agagattcat gccacaagat ccccataatt agtacagtaa     480
ttaattcgat ccttttacta cttcaagatg actacgggcc cggattagtc tacttccctt     540
gctataataa tactgtacaa gttgtaaaaa aaaaaaaaaa aaaaaaaa                  588

<210> SEQ ID NO 8
<211> LENGTH: 129
<212> TYPE: PRT
<213> ORGANISM: Triticum aestivum

<400> SEQUENCE: 8

Leu Ile Val Leu Glu Pro His Gly Gly Leu Met Ala Thr Ile Pro Thr
 1               5                  10                  15

Ala Ala Thr Pro Tyr Pro His Arg Ser Gly Val Leu Tyr Ile Ile Gln
             20                  25                  30

Tyr Ile Ala Phe Trp Gln Gly Asp Gly Gly Thr Ala Ala Thr Thr Trp
         35                  40                  45

Leu Gly Ser Phe Tyr Asp Phe Met Gly His Tyr Val Ser Ser Asn Pro
     50                  55                  60

Arg Gln Ala Tyr Val Asn Phe Arg Asp Leu Asp Ile Gly Gln Asn Ala
 65                  70                  75                  80

Val Ser Asp Asp Leu Ser Thr Thr Ser Gln Ser Gly Lys Val Trp Gly
                 85                  90                  95

Glu Arg Tyr Phe Met Ser Asn Tyr Gln Arg Leu Ala Ser Val Lys Ala
            100                 105                 110

Ala Val Asp Pro Met Asp Tyr Phe Arg Asn Glu Gln Ser Ile Pro Pro
            115                 120                 125

Leu
```

16. The polynucleotide of claim 1 wherein the polynucleotide encodes a polypeptide of SEQ ID NO:6.

17. An isolated complement of the polynucleotide of claim 1, wherein (a) the complement and the polynucleotide consist of the same number of nucleotides, and (b) the nucleotide sequences of the complement and the polynucleotide have 100% complementarity.

* * * * *